(12) United States Patent
Lacson et al.

(10) Patent No.: US 10,959,648 B2
(45) Date of Patent: Mar. 30, 2021

(54) WEARABLE WORD COUNTER

(71) Applicant: The University of Chicago, Chicago, IL (US)

(72) Inventors: Alvin Lacson, Portola Valley, CA (US); Jill Desmond, Portola Valley, CA (US); Andy Turk, Portola Valley, CA (US); Jon Boggiano, Portola Valley, CA (US); Chris Boggiano, Portola Valley, CA (US); Nolan Danley, Portola Valley, CA (US); Arbind Thakur, Portola Valley, CA (US)

(73) Assignee: The University of Chicago, Chicago, IL (US)

( * ) Notice: Subject to any disclaimer, the term of this patent is extended or adjusted under 35 U.S.C. 154(b) by 101 days.

(21) Appl. No.: 16/168,439

(22) Filed: Oct. 23, 2018

(65) Prior Publication Data

US 2019/0117126 A1 Apr. 25, 2019

Related U.S. Application Data

(63) Continuation-in-part of application No. 15/191,688, filed on Jun. 24, 2016, now Pat. No. 10,134,424.

(Continued)

(51) Int. Cl.
*G10L 15/00* (2013.01)
*G10L 15/04* (2013.01)
(Continued)

(52) U.S. Cl.
CPC .......... *A61B 5/1118* (2013.01); *A61B 5/0022* (2013.01); *A61B 5/4809* (2013.01); *A61B 5/6898* (2013.01); *A61B 5/7225* (2013.01); *A61B 5/7235* (2013.01); *A61B 5/7264* (2013.01); *G10L 25/48* (2013.01);
(Continued)

(58) Field of Classification Search
None
See application file for complete search history.

(56) References Cited

U.S. PATENT DOCUMENTS 6,185,527 B1 2/2001 Petkovic
6,208,970 B1 3/2001 Ramanan
(Continued)

FOREIGN PATENT DOCUMENTS

DE 10212128 A1 10/2003

OTHER PUBLICATIONS

Betty Hart & Todd R. Risley, Meaningful Differences in the Everyday Experience of Young American Children (pp. vii, 21-49, 58-59, 64-67, 72-75, 132-33, 234-35, 238-41), 1995, Paul H. Brookes Publishing Co., Baltimore, MD.

*Primary Examiner* — Satwant K Singh
(74) *Attorney, Agent, or Firm* — Travis R. Banta; TechLaw Ventures, PLLC

(57) ABSTRACT

This disclosure generally relates to a system for communicating data generated by a wearable device to one or more server devices for analysis. The one or more server devices may transmit activity level data, or a graphical representation thereof, for a wearer of a wearable device to a device associated with a healthcare provider. The activity level data may include one or more of an active minutes element, a television time element, a word count element, a sleep duration element and a reading duration and score element.

15 Claims, 3 Drawing Sheets

Related U.S. Application Data

(60) Provisional application No. 62/184,291, filed on Jun. 25, 2015.

(51) Int. Cl.

| | | |
|---|---|---|
| *A61B 5/11* | (2006.01) | |
| *G10L 25/48* | (2013.01) | |
| *A61B 5/00* | (2006.01) | |
| *G16H 40/67* | (2018.01) | |
| *G10L 25/66* | (2013.01) | |
| *G10L 25/78* | (2013.01) | |

(52) U.S. Cl.
CPC ............. *G10L 25/66* (2013.01); *G16H 40/67* (2018.01); *A61B 5/746* (2013.01); *A61B 2560/0242* (2013.01); *A61B 2560/0412* (2013.01); *A61B 2562/0204* (2013.01); *A61B 2562/0219* (2013.01); *G10L 25/78* (2013.01)

(56) References Cited

U.S. PATENT DOCUMENTS

| | | | | |
|---|---|---|---|---|
| 6,990,445 | B2 | 1/2006 | Ky | |
| 8,700,012 | B2* | 4/2014 | Ferren | G06F 3/0418 |
| | | | | 455/414.2 |
| 8,976,941 | B2 | 3/2015 | Kim | |
| 9,148,483 | B1* | 9/2015 | Molettiere | H04L 43/50 |
| 9,190,060 | B2 | 11/2015 | Nonaka | |
| 9,369,365 | B2* | 6/2016 | Molettiere | H04L 67/10 |
| 9,390,709 | B2 | 7/2016 | Nonaka | |
| 9,392,941 | B2* | 7/2016 | Powch | A61B 5/0024 |
| 9,459,454 | B1* | 10/2016 | The | A63F 13/211 |
| 9,530,401 | B2 | 12/2016 | Kim | |
| 9,548,046 | B1 | 1/2017 | Boggiano | |
| 9,681,827 | B2* | 6/2017 | Huang | G16H 40/67 |
| 9,712,629 | B2* | 7/2017 | Molettiere | G06F 3/0486 |
| 9,763,571 | B2* | 9/2017 | Kozloski | A61B 3/0025 |
| 9,962,118 | B2* | 5/2018 | Kozloski | A61B 5/4064 |
| 9,968,287 | B2* | 5/2018 | Kozloski | A61B 5/7271 |
| 10,134,424 | B2* | 11/2018 | Lacson | G09B 21/00 |
| 10,789,939 | B2* | 9/2020 | Lacson | G10L 15/22 |
| 2002/0169583 | A1 | 11/2002 | Gutta | |
| 2003/0220788 | A1 | 11/2003 | Ky | |
| 2007/0185704 | A1 | 8/2007 | Yoshimura | |
| 2009/0043581 | A1 | 2/2009 | Abbott | |
| 2010/0217591 | A1 | 8/2010 | Shipgel | |
| 2013/0322215 | A1 | 12/2013 | Du | |
| 2014/0123311 | A1* | 5/2014 | Pegg | G06F 21/10 |
| | | | | 726/27 |
| 2014/0244255 | A1 | 8/2014 | Nonaka | |
| 2016/0278633 | A1* | 9/2016 | Kozloski | A61B 3/112 |
| 2016/0278666 | A1* | 9/2016 | Kozloski | A61B 5/4064 |
| 2016/0278686 | A1* | 9/2016 | Kozloski | A61B 3/112 |
| 2016/0371240 | A1* | 12/2016 | McKaughan | G06F 40/205 |
| 2016/0372135 | A1* | 12/2016 | Lee | G10L 19/06 |
| 2019/0122652 | A1* | 4/2019 | Lacson | G10L 15/02 |

* cited by examiner

WEARABLE WORD COUNTER

This application is a Continuation-In-Part of and claims priority to U.S. patent application Ser. No. 15/191,688, filed Jun. 24, 2016, which claims priority to U.S. Provisional Patent Application No. 62/184,291, filed on Jun. 25, 2015, which are incorporated by reference in their respective entireties.

BACKGROUND

1. Technical Field

This disclosure relates generally to a wearable device. More specifically, the device disclosed herein relates to a device that may be worn by a user to count a number of words heard by or spoken to the user over a period of time.

2. Description of the Related Art

Child rearing and development is often one of the most daunting tasks that new parents face. However, many parents simply lack the knowledge and tools to objectively track a child's development in the child's early years when brain development is most rapid. Moreover, recent studies have shown a correlation between brain development in young children and the degree of interaction they have with parents and others. Specifically, a high degree of correlation exists between the quantity of words spoken to a baby and brain development in children younger than three years old. Given that the number of words spoken to a baby predicts a baby's intelligence and that a person's intelligence stabilizes for life by pre-school, the number of words spoken to a child between birth and age three largely sets the child's mental ability trajectory for the child's lifetime.

In order to track the number of words spoken to children for these studies, researchers used cassette tapes or digital speech recorders to record conversations in the homes of young children. Once the recordings were completed, researchers tediously transcribed the recordings and manually counted each word heard by or spoken to a young child. This method of counting words spoken to a child is profoundly inefficient in terms of effort and time effectiveness. While these technologies made it possible to manually count the words spoken to a child they are inadequate to do any more than make a recording of conversations for later transcription. Other more rudimentary methods for counting the number of words heard by or spoken to a child have also included an observer manually counting words as the words are spoken to a child.

One difficulty in monitoring the number of words spoken to a child is that between birth and three years of age, most children become ambulatory and move away from, and out of recording range of, conventional stationary recording devices. However, with the advent of wearable devices, also known as "wearables," mobile processing power has been substantially increased allowing previously stationary devices to become portable. As processing power per unit of physical space has increased, wearables have gained in popularity with the general public by incorporating processing power into articles of clothing or devices that attach to the head, hands, feet, arms, legs, or other body parts of their users. Several examples of wearable devices include a calculator wristwatch, eye glasses that incorporate heads-up displays, ear muffs or hats that incorporate head phones or ear buds, smart watches, smart headbands, smart pedometers, and a host of other implementations that provide various users with desired information or entertainment. Many wearable devices have been implemented as health care or health monitoring devices and are used to monitor heart rate, blood pressure, physical activity levels, body temperature, and other physical indications for the ill and for high performance athletes.

It is therefore one object of this disclosure to provide a wearable device that counts the number of words spoken to or heard by a user in real-time. Another object of this disclosure is to provide a wearable word counting device to count the number of words spoken to or heard by a user and transmit a real-time word count to another device. Another object of this disclosure is to provide a wearable device that streams information to a remote device with greater processing power. Another object of this disclosure is to provide a wearable device capable of performing speech analysis in a low-power environment.

SUMMARY

Consistent with embodiments disclosed herein, a system for providing child activity data to a health care provider via a word counter device. The word counter device monitors the number of words spoken to a child, the child's activity level, and the child's routine and collects corresponding data. The word counter device may connect directly or indirectly to a server computer which provides data collected by monitoring the child to a healthcare provider dashboard.

Also disclosed herein is a system that provides the healthcare provider with information about a child's activity. The system receives data about the child and provides the data as a graphical user interface on a screen of a device associated with the healthcare provider for review.

BRIEF DESCRIPTION OF THE DRAWINGS

The accompanying drawings illustrate an embodiment of a wearable word counter.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
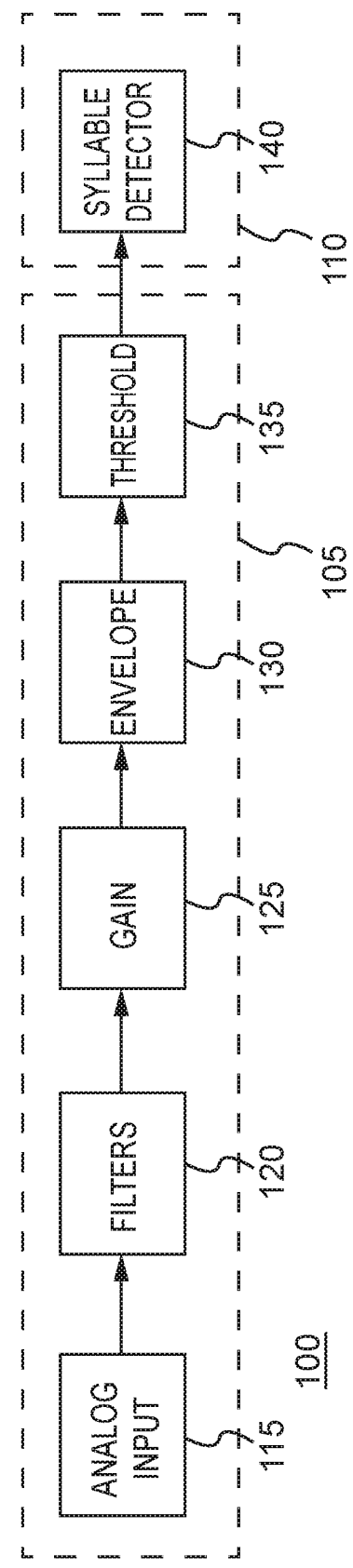
FIG. 1 illustrates a block circuit diagram of the wearable word counter.

FIG. 1 illustrates a block circuit diagram of wearable word counter 100. Wearable word counter 100 includes an analog low power circuit 105 that is coupled to a digital microcontroller circuit 110. In one embodiment, wearable word counter 100 includes a battery, not shown, which supplies power to both analog low power circuit 105 and digital microcontroller circuit 110. During use, the battery within wearable word counter 100 supplies power sufficient for analog low power circuit 105 and digital microcontroller circuit 110 to operate for an extended time period. For example, in one mode of operation, the battery within wearable word counter 100 supplies sufficient power for wearable word counter 100 to operate for a period of up to a week. The battery within wearable word counter 100 may be a rechargeable battery, allowing the battery within wearable word counter 100 to be recharged during periods of non-use.

In use, wearable word counter 100 is portable. For example, wearable word counter 100 may be attached to a user, such as a child, or, alternatively, attached to the user's clothing. Thus, in one embodiment, wearable word counter 100 may be attached to the user or the user's clothing in a way that does not restrict the ability of the user to move or play. Wearable word counter 100 may further be positioned on the user or user's clothing such that it may be unobstructed to the aural environment of the user to whom it is attached. Wearable word counter 100 may move with the user as the user travels in a physical environment. In one embodiment, wearable word counter 100 may be removed when the user sleeps because a user is generally not perceptive of sounds during sleep.

Because wearable word counter 100 is portable and powered by a battery, it is advantageous that battery power consumed by wearable word counter 100 is minimized. Accordingly, wearable word counter 100 reduces power consumption by implementing analog low power circuit 105. Analog low power circuit 105 consumes far less battery power than other technologies, such as a digital signal processor, and others, while providing sufficient functionality to detect individual words spoken to a user of wearable word counter 100. Thus, at least one advantage of wearable word counter 100 is that analog low power circuit 105 consumes very little battery power. In general, a physical size of a battery is proportional to the amount of electrical voltage and electrical current produced by the battery. Accordingly, because wearable word counter 100 utilizes analog low power circuit 105, the physical size of wearable word counter 100 may be substantially smaller than a similar device that utilizes digital signal processing technology. A smaller physical size for wearable word counter 100 is less cumbersome to a user, interferes less with the user's movement, and is lighter allowing the user to bear the weight of wearable word counter 100 more easily. Wearable word counter 100 may be implemented with each of the elements shown in FIG. 1 in a single housing.

Figure 2:
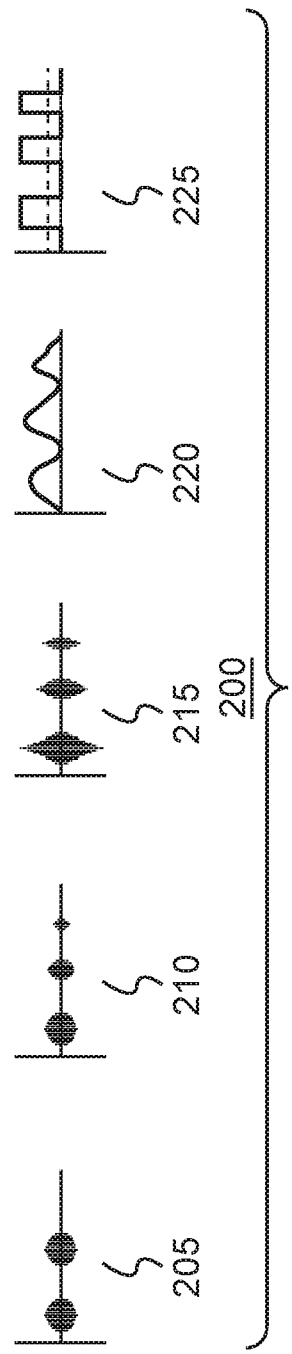
FIG. 2 illustrates a series of waveforms representative of various stages of the block circuit diagram illustrated in FIG. 1.

Analog low power circuit 105 within wearable word counter 100 includes an analog input receiver 115, linear analog filters 120, a gain amplifier stage 125, an envelope detector 130, and a threshold detector 135. FIG. 2 shows a series of waveforms 200 that are used herein to explain the elements of analog low power circuit 105.

For example, analog input receiver 115 may be implemented as a microphone installed within wearable word counter 100 that receives analog input, such as a speech signal. In this embodiment, the microphone within analog input receiver 115 may be positioned within wearable word counter 100 in such a way as to be relatively unobstructed from the user's aural environment. That is to say, the microphone may be positioned within wearable word counter 100 such that the microphone will detect any spoken words that would be heard by the user, for example. Audio input waveform 205 shows a representation of three syllables spoken by, for example, a parent to a small child as detected by a microphone within analog input receiver 115 shown in FIG. 1.

After analog input receiver 115 receives analog input, one or more linear analog filters 120 remove undesirable portions of the analog input signal. Although referred to in the plural, linear analog filters 120 may be implemented as a single filter or in combinations of various filters. Linear analog filters 120 may be implemented as low pass filters, high pass filters, all pass filters, band pass filters, band reject filters, and any other type of analog filter. Linear analog filters 120 may, for example, be implemented to remove portions of the analog input that fall outside the hearing ability of a human being. For example, linear analog filters may filter out any portions of analog input above 20 kHz, leaving the portion of the analog input between 0 Hz and 20 kHz. Linear analog filters 120 may be implemented in such a way as to remove noise from the analog input. Linear analog filters 120 may be further implemented in such a way as to remove portions of the analog input that would be inconsistent with human speech. For example, the frequency range of voiced speech typically occurs in the range of 100 Hz to 3 kHz. Linear analog filters 120 may be implemented to remove any portion of the analog input that falls outside the range of 100 Hz to 3 kHz, for example. Any particular implementation of linear analog filters 120 may be implemented to meet any desirable range of analog input received by analog input receiver 115. Filtered audio input waveform 210 of FIG. 2 shows the same three syllables that are shown in audio input waveform 205 after those words have been subjected to filtering via linear analog filters 120.

Once filtering is complete, a filtered signal is produced by linear analog filters 120 and is provided to gain amplifier stage 125. Gain amplifier stage 125 is used to amplify and enhance the filtered signal. Amplifying the filtered signal increases the amplitude of the filtered signal and makes the filtered signal large enough to measure or compare to a threshold, as will be discussed below. For example, amplified filtered waveform 215 shown in FIG. 2 shows clearly three distinct syllables that were received as analog input, filtered by the linear analog filters 120, and amplified in gain amplifier stage 125. This amplified signal is provided to envelope detector 130.

Envelope detector 130 operates as a waveform smoothing function on the amplified signal provided to envelope detector 130. Generally, a capacitor is slowly charged and discharged by the amplified signal, which produces a waveform similar to that shown as envelope waveform 220, shown in FIG. 2. Thus, envelope detector 130 removes each frequency spike of the original analog input in favor of providing a smoothed waveform representative of the three syllables originally spoken to the user of wearable word counter 100. Envelope detector 130 provides this smoothed signal to threshold detector 135. The term "smooth waveform" or "smoothed waveform" means a waveform substantially free from frequency spikes. One example of a smoothed waveform is shown as envelope waveform 220, shown in FIG. 2.

Threshold detector 135 applies a threshold level to the smoothed signal to determine what portions of the analog input do and do not correspond to a spoken syllable. In one embodiment, threshold detector 135 may be implemented as a voltage detector or a current detector implemented as voltage comparators. Other types of threshold detectors are possible. In practice, threshold detector 135 detects any portion of the smoothed signal generated by envelope detector 130 that exceeds a particular amplitude (current or voltage). As shown in FIG. 2, threshold waveform 225 denotes that the smoothed signal shown in envelope waveform 220 exceeds the threshold amplitude in three portions of threshold waveform 225. Threshold detector 135 converts the smoothed signal into a square wave, showing the three syllables spoken to the user and eliminating any portion of the smoothed signal that does not meet or exceed the particular amplitude determined to correspond to a syllable of speech. The square wave is provided by threshold detector 135 to syllable detector 140.

Syllable detector 140 is implemented by a processor in digital microcontroller circuit 110. The processor in digital microcontroller circuit 110 within wearable word counter 100 can include a combination of one or more application programs and one or more hardware components. For example, application programs may include software modules, sequences of instructions, routines, data structures, display interfaces, and other types of structures that execute operation. Further, hardware components may include a combination of processors, microcontrollers, busses, volatile and non-volatile memory devices, non-transitory computer readable memory device and media, data processors, control devices, transmitters, receivers, antennas, transceivers, input devices, output devices, network interface devices, and other types of components that are apparent to those skilled in the art.

Syllable detector 140 receives the square wave from threshold detector 135 and compares the square wave received from threshold detector 135 against a square wave duration threshold. Any square wave with a duration less than a minimum time duration threshold is discarded. Similarly, any square wave with a duration greater than a maximum time duration threshold is also discarded. Any square wave with a duration greater than the minimum time duration threshold and less than the maximum time duration threshold is representative of a syllable spoken to a user of wearable word counter 100. Accordingly, syllable detector 140 aggregates the number of syllables spoken to the user. Typically, adults speak to babies using monosyllabic words. Thus, the syllable to counted word ratio spoken to a baby may be approximately 1:1. However, as a child grows, adult speech directed to the child gains complexity, using both monosyllabic and polysyllabic words. Thus, as a baby grows into a child, the number of syllables per individual word spoken to the child increases. Accordingly, syllable detector 140 may monitor the age of the user and adjust the syllable to counted word ratio to count the number of words spoken to the user of wearable word counter 100 as a child grows from infancy.

For example, adults speaking to babies may not use complete sentences. An adult speaking to a baby may point to a dog and say "dog, dog, dog" while an adult speaking to a toddler may point to a dog and say "do you see the furry puppy?" In such a case, the adult's speech directed to a toddler is substantially more complex than the adult's speech directed to the baby. Accordingly, wearable word counter 100 may adjust the counting of words to account for more complex speech by adjusting the syllable to counted word ratio. For a baby younger than 6 months old, in one hypothetical example, wearable word counter 100 may use a syllable to counted word ratio of one syllable to one counted word (i.e., one syllable is counted as one word). For a baby older than 6 months, in another hypothetical example, wearable word counter 100 may use a syllable to counted word ratio of 1.5 syllables to one counted word (i.e., for every 1.5 counted syllables, one word is counted). For babies older than a year, in another hypothetical example, wearable word counter 100 may use a syllable to counted word ratio of 2 syllables to one counted word (i.e., for every 2 counted syllables, one word is counted). Syllable detector 140 may adjust this syllable to counted word ratio based on the age of the user of wearable word counter 100.

Syllable detector 140 constantly monitors speech directed to the user of wearable word counter 100 and counts the syllables detected. Once syllable detector 140 applies the syllable to counted word ratio, a number of words spoken to the user is determined. In one embodiment, this number of words spoken to the user may be transmitted by wearable word counter 100 to a mobile device. Any mobile device may be suitable for receiving information from wearable word counter 100. Conventional mobile devices include devices that are capable of running a software application, such as a smart phone, a tablet, a personal computer, a desktop computer, a music storage and playback device, a personal digital assistant, or any other device capable of implementing a software application.

In one embodiment, digital microcontroller circuit 110 (and/or syllable detector 140) may automatically adjust an amplification and a threshold level for received audio input based on ambient noise in a particular aural environment. For example, in a noisy room, digital microcontroller circuit 110 may sample the aural environment to determine a "noise floor" for that environment. The noise floor may also be referred to as ambient noise. During speech, the ambient noise is increased. In order to recognize speech in relatively noisy aural environments, digital microcontroller circuit 110 may adjust the amplification and threshold levels discussed above such that only speech directed to the user of wearable word counter 100 meets or exceeds the adjusted threshold level. This automatic adjustment ensures that the syllable count remains accurate because ambient noise falls short of meeting an automatically set threshold for a particular aural environment. Thus, ambient noise is not reflected in the syllable count.

In another embodiment, wearable word counter 100 may transmit information to one or both of a mobile device and a non-mobile device. For example, wearable word counter 100 may be provided with a docking station designed to remain tethered to a non-mobile power supply. The docking station may operate using alternating current power supplied from an electrical outlet in, for example, a home. In one embodiment, the docking station may be configured to recharge the battery or batteries within wearable word counter 100 when the docking station is connected to wearable word counter 100. The docking station may receive information from wearable word counter 100 wirelessly, through a wired connection, and/or through a corresponding male and female connector disposed within wearable word counter 100 and the docking station. The docking station may have a separate ability to connect to a mobile device, a server, a cloud computer, or any other device using a wired or wireless connection to provide information received from wearable word counter 100 to other devices. The mobile device may display information, including word count information, received from wearable word counter 100. The docking station may further implement any functionality of the mobile device described herein.

In one embodiment, wearable word counter 100 may connect to the mobile device or to the non-mobile device using a wireless communication connection. For example, a wireless communication connection may be implemented using a Bluetooth wireless communication link. Numerous other types of communication links may also be implemented including Wi-Fi, ZigBee, Z-Wave, RF4CE, Ethernet, telephone line, cellular channels, or others that operate in accordance with protocols defined in IEEE (Institute of Electrical and Electronics Engineers) 802.11, 801.11a, 801.11b, 801.11e, 802.11g, 802.11h, 802.11i, 802.11n, 802.16, 802.16d, 802.16e, or 802.16m using any network type including a wide-area network ("WAN"), a local-area network ("LAN"), a 2G network, a 3G network, a 4G network, a Worldwide Interoperability for Microwave Access (WiMAX) network, a Long Term Evolution (LTE) network, Code-Division Multiple Access (CDMA) network, Wideband CDMA (WCDMA) network, any type of satellite or cellular network, or any other appropriate protocol to facilitate communication between wearable word counter 100 and the mobile device.

In one embodiment, the mobile device may be used to interface with wearable word counter 100. For example, in addition to receiving a real-time transmission of the number of words spoken to a user of wearable word counter 100, the mobile device may additionally allow another user, such as a parent of a child wearing wearable word counter 100, to make adjustments in the settings of wearable word counter 100. For example, the parent may manually adjust the syllable to counted word ratio to more accurately reflect the level of speech complexity heard by the child for a particular duration of time. For example, a parent may use a mobile device to adjust the syllable to counted word ratio down if a toddler were to experience a play date with other toddlers for the duration of the playdate (because other toddlers will use less complex speech to interact with other toddlers). In another embodiment, the mobile device recommends a particular syllable to counted word ratio to be implemented by wearable word counter 100 during a particular time.

One benefit of connecting wearable word counter 100 to a mobile device is accessing the enhanced processing power of the mobile device. Mobile devices typically have much more advanced processing capabilities than wearable word counter 100, which allows for more complex analysis of speech and speech patterns. Accordingly, wearable word counter 100 may, in addition to counting the number of words spoken to a child, stream the analog input to the mobile device for more complex analysis in a compressed or uncompressed format. In one embodiment, wearable word counter 100 may apply initial filtering and amplification to the analog input with linear analog filters 120 and gain amplifier stage 125 before streaming a filtered and amplified representation of the analog input to the mobile device. In another embodiment, wearable word counter 100 may intermittently stream the analog input at different times during use in order to provide the mobile device of an averaged sample of the analog input. In one embodiment, wearable word counter 100 records analog input and transmits the analog input as an analog signal to the mobile device via the wireless communication connection.

In another embodiment, the mobile device records an analog signal representative of voiced speech directed to a user of wearable word counter 100 provided over the wireless communication connection by wearable word counter 100. The mobile device may transmit the recorded analog signal to a server or to a cloud computer for more advanced speech processing or perform speech analysis in the mobile device. In another embodiment, wearable word counter 100 may stream an analog signal representative of voiced speech directed to a user of wearable word counter 100 over a wireless communication connection directly to a cloud computer, without transmitting the analog signal through the mobile device. In these ways, more complex analysis of the speech heard by or spoken to the user may be performed. This more complex analysis may provide a mobile phone user (or a cloud computer user) with information such as the number of times a user of wearable word counter 100 has heard a particular word or identify commonly used conversational terms, identify the language or languages spoken to the user of wearable word counter 100, and other similar analysis. The mobile device may also update the firmware within wearable word counter 100 via the wireless communication connection between the mobile device and wearable word counter 100.

Finally, wearable word counter 100 may further include a light sensor and an accelerometer. In one embodiment, wearable word counter 100 may determine, via a light sensor, that the user is watching television based on the flickering light emitted by the television. Wearable word counter 100 may exclude words that are detected during periods when the light sensor detects the flickering light emitted by a television. In one embodiment, a light sensor may further be used to detect an ambient light level in the environment around wearable word counter 100. Wearable word counter 100 may determine that a certain level of light, or lack thereof, indicates that the user of wearable word counter 100 may be asleep or going to sleep. Accordingly, wearable word counter 100 may determine, based on the detected ambient level of light, that no words are likely to be spoken to the user and enter an off state or a power stand-by state or discontinue streaming audio information in order to save battery power. In another embodiment, wearable word counter 100 may infer a state of a user based on the user's movement, as detected by the accelerometer. If the user is moving, for example, wearable word counter 100 may stream audio to the mobile device. However, if the user is not moving, as detected by the accelerometer, wearable word counter 100 may infer that the user is asleep and stop the streaming audio information until the user awakes. Wearable word counter may also enter an off state or a power stand-by state in order to save battery power during periods when the user's movements are less frequent or reduced.

Figure 3:
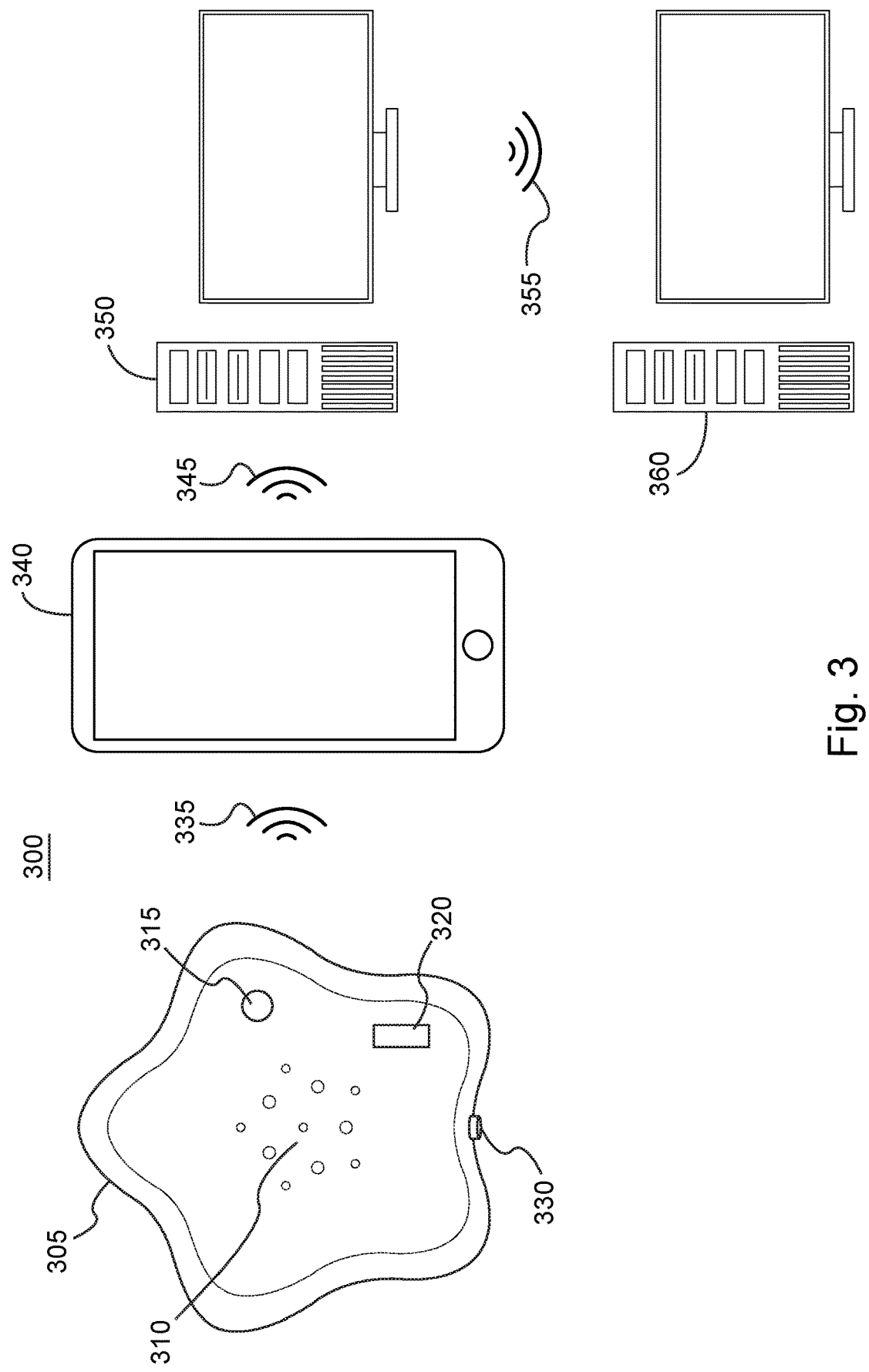
FIG. 3 illustrates an exemplary system for communicating child activity data to a healthcare provider user interface.

FIG. 3 illustrates an exemplary system 300 for communicating child activity data to a healthcare provider user interface. System 300 includes a word counter 305 which may, or may not, be formed in a fanciful shape and may be worn by a child, who may be interchangeably referred to as a "wearer of a wearable word counter" or "wearer of a wearable device." Wearable word counter 305 is shown as being formed in the shape of a star, in the example of FIG. 3, although other shapes are possible. Wearable word counter 305 may include a number of perforations to accommodate a microphone 310 disposed within wearable word counter 305. As previously discussed, wearable word counter 305 may further include a light sensor 315 disposed within wearable word counter 305 that provides information and input about the amount of light in the environment around wearable word counter 305 to a processor disposed within wearable word counter 305, such as a processor disposed within digital microcontroller circuit 110 discussed above with respect to FIG. 1. Wearable word counter 305 may further include an accelerometer 320 disposed within wearable word counter 305 that provides information and input about the amount or total amount of movement in three dimensional axes (X, Y, and Z in the Cartesian sense) associated with a wearer of wearable word counter 305 to a processor disposed within wearable word counter 305, such as a processor disposed within digital microcontroller circuit 110. It is assumed that, when worn, movement of wearable word counter 305 is commensurate with movement of a wearer of wearable word counter 305. Wearable word counter 305 may further include a button 330 that allows a user to interface with wearable word counter 330 directly, or via a mobile device.

In one embodiment, wearable word counter 305 may employ microphone 310 to record one or more words spoken in an environment of a wearer of wearable word counter 305. Further, wearable word counter 305 may employ microphone 310 in combination with light sensor 315 and accelerometer 320 to determine the quality and intentionality of the one or more spoken words. For example, in one embodiment, wearable word counter 305 itself, or in combination with a mobile device, may identify whether or not a wearer of wearable word counter 305 is moving via accelerometer 320 and how much light is in the wearer of the wearable word counter's environment.

In this manner, a wearable word counter 305 may identify that wearer of the wearable word counter 305 is likely to be awake because there is a bright light in the wearer of the wearable word counter's environment, and substantial movement is being detected via accelerometer 320. Given that a wearer of wearable word counter 305 is likely to be awake because of the level of light and the level of movement associated with the wearer of wearable word counter 305, wearable word counter 305 may determine, using the techniques described herein, that a speaker is speaking to or directing speech to the wearer of wearable word counter 305. Alternatively, wearable word counter 305 may detect speech, low light, and little movement via microphone 310, light sensor 315, and accelerometer 320, respectively and determine that the wearer of wearable word counter 305 is likely asleep. Based on the determination that the wearer of wearable word counter 305 is likely asleep, wearable word counter 305 may determine that it should not count the number of words spoken to the wearer of wearable word counter 305. In other words, speech that is spoken to the wearer of wearable word counter 305 when the wearer of wearable word counter 305 is asleep may be identified as low quality speech or speech that is not intentionally spoken to or directed to a child and may, therefore, not be counted as words heard by the wearer of wearable word counter 305.

Wearable word counter 305 may further detect repeatable trends in a wearer of wearable word counter's daily schedule in order to identify speech that is intended to be spoken to the child at a particular time of day. In other words, if wearable word counter 305 detects that the amount of light in the environment of a wearer of wearable word counter 305 decreases every afternoon at 2:00 and further detects that the amount of movement associated with the wearer of wearable word counter 305 substantially decreases every afternoon at 2:00, wearable word counter 305 may determine that 2:00 is a likely nap time for the wearer of the wearable word counter. In response, wearable word counter 305 may determine that speech detected during periods associated with these repeatable trends should not be counted as speech spoken to a wearer of wearable word counter 305. Alternatively, wearable word counter 305 may detect that the amount of light in the environment of the wearer of wearable word counter 305 increases every morning around 9:30 and further detects that the amount of movement associated with a wearer of wearable word counter 305 substantially increases every morning at 9:30. In response, wearable word counter 305 may determine that the wearer of wearable word counter 305 wakes up each morning at approximately 9:30 and begin identifying and counting words spoken to the wearer of wearable word counter 305.

In FIG. 3, system 300 may allow wearable word counter 305 to connect to a secondary device 340 with a wired or wireless connection 335. For the purposes of explanation with respect to FIG. 3, a low power environment for wearable word counter 305 is shown. However, it may also be possible for wearable word counter 305 to send data directly to and receive data directly from one or more server computing devices 350 without the need for secondary device 340. While such an implementation would negatively affect battery life inside wearable word counter 305, this high-power implementation is also possible and would render secondary device 340 unnecessary. However, in a preferred embodiment, secondary device 340 interfaces both with wearable word counter 305 and one or more server computing devices 350, as discussed below.

Any suitable wireless protocol disclosed above may be implemented to connect wearable word counter 305 to secondary device 340 with connection 335. In FIG. 3, secondary device 340 may be implemented as a mobile device, such as mobile device discussed above with respect to FIG. 1 and FIG. 2. However, secondary device 340 may be implemented as a charging station for wearable word counter 305, or another device that may interface with wearable word counter 305. Other implementations of secondary device 340 may include devices that are capable of running a software application, such as a smart phone, a tablet, a personal computer, a desktop computer, a music storage and playback device, a personal digital assistant, or any other device capable of running a software application.

In the example of FIG. 3, wearable word counter 305 may obtain various child activity data, which includes data representative of a child's activity for a particular time period. In one example, child activity data may include data representative of the number of minutes a child is detected to be active in a day, a number of words spoken to the child in a day, an amount of time a child spent watching television in a day, a duration of sleep in a day, a duration of a reading session, and a reading session score. In short, any data collected by wearable word counter 305 via microphone 310, light sensor 315, or accelerometer 320 may be communicated to secondary device 340 via connection 335.

Secondary device 340 (or wearable word counter 305 in an optional high-power embodiment) may connect to one or more server computing devices 350 using a wired or wireless connection 345. Any suitable wired connection or wireless protocol disclosed above may implement connection 345 between secondary device 340 (or wearable word counter 305 in an optional high-power environment) and one or more server computing devices 350. The one or more server computing devices may include cloud computers, super computers, mainframe computers, application servers, catalog servers, communications servers, computing servers, database servers, file servers, game servers, home servers, proxy servers, stand-alone servers, web servers, combinations of one or more of the foregoing examples, and any other computing device that may be used to analyze, process, interpret, receive, or transmit information representative of or concerning child activity data. The one or more server computing devices may include software and hardware modules, sequences of instructions, routines, data structures, display interfaces, and other types of structures that execute server computer operations. Further, hardware components may include a combination of Central Processing Units ("CPUs"), buses, volatile and non-volatile memory devices, storage units, non-transitory computer-readable storage media, data processors, processing devices, control devices, transmitters, receivers, antennas, transceivers, input devices, output devices, network interface devices, and other types of components that are apparent to those skilled in the art. These hardware components within one or more server computing devices may be used to execute the various methods or algorithms disclosed herein, and interface with wearable word counter 305 or secondary device 340 and provider device 360.

Once one or more server computing devices 350 has received child activity data generated by wearable word counter 305, one or more server computing devices 350 may analyze or process the child activity data to provide information about an activity level of the child to a health care provider. The term "activity level" is to be interpreted broadly to include, but not limited to, physical activity, educational activity, word counts, time spent watching television, sleep durations, reading quality assessments, and reading session durations. Any information collectible by wearable word counter 305 may be used to generate "activity level" information. This activity level determined by the one or more server computing devices 350 (or data associated with the determined activity level) may be transmitted from one or more server computing devices 350 to provider device 360 for graphical representation either directly or indirectly using a wired or wireless connection or through the Internet to a provider device 360. As an example, provider device 360 may be implemented by any device capable of running a software application, such as a smart phone, a tablet, a personal computer, a desktop computer, a music storage and playback device, a personal digital assistant, or any other device capable of implementing a software application.

Provider device 360 may be associated with a health care provider for a child. In one embodiment, the child's doctor, therapist, nurse, doctor's office staff, or any other medical support staff may obtain the child activity data for a child cared for by a doctor. The child activity data may be presented in a graphical user interface via a monitor/screen associated with provider device 360 or may be otherwise provided to a doctor.

Figure 4:
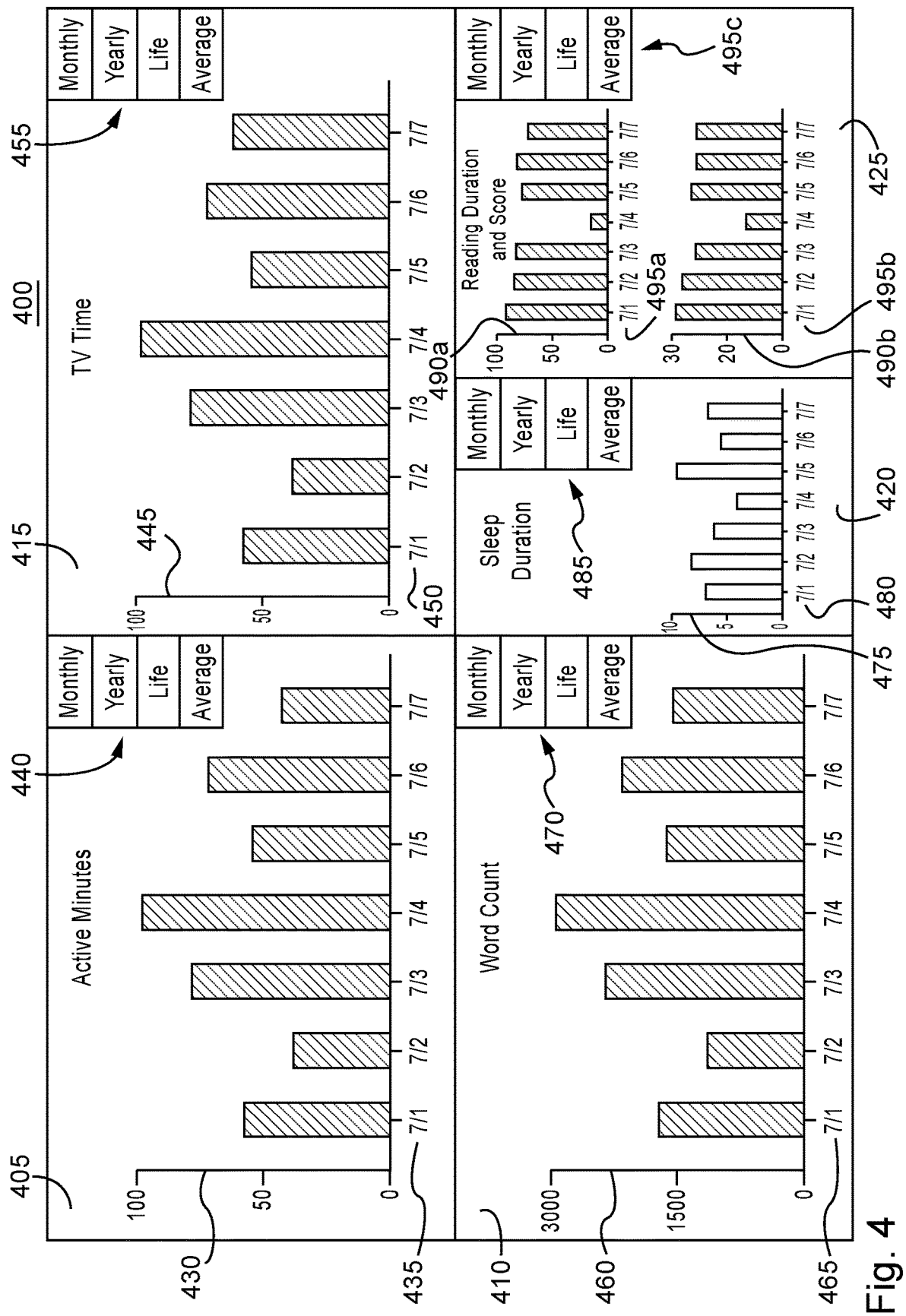
FIG. 4 illustrates an exemplary health care provider graphical user interface.

FIG. 4 illustrates an exemplary health care provider graphical user interface 400. Graphical user interface 400 may be provided by a monitor/screen associated with provider device 360, shown in FIG. 3. Graphical user interface 400 includes a plurality of visual element blocks, including active minutes element 405, word count element 410, television ("TV") time element 415, sleep duration element 420, and a reading duration and score element 425. Each one of these plurality of elements will be discussed in detail below.

Active minutes element 405 may include a graphical representation of a number of minutes a child is determined to be active as identified by wearable word counter 305, shown in FIG. 3. Active minutes element 405 may include a minutes axis 430 representative of a number of minutes and a date axis 435 representative of a date. As shown in FIG. 4, each date on date axis 435 has an associated representation of a number of minutes of activity or active play time for a child associated with wearable word counter 305 on a per-day basis. For example, on July 1, a child wearing wearable word counter 305 is active for approximately 60 minutes during the day of July 1.

Active minutes element 405 may further include one or more interface elements 440 which allow a user of graphical user interface 400 to scale date axis 435. Exemplary interface elements 440 include a button to scale date axis 435 to show a monthly total of active minutes, a yearly total of active minutes, a life total of active minutes for the life of the wearer of wearable word counter 305, or an average number of active minutes for the wearer of wearable word counter 305. Other interface elements 440 may include a button to scale date axis 435 to show a weekly total of active minutes or may allow a user to selectively scale date axis 435 to a specific selectable customized time period between two different user selected dates.

Word count element 410 may include a graphical representation of the number of words spoken to a child as identified by wearable word counter 305, shown in FIG. 3. Word count element 410 may include a word count axis 460 representative of a number of words spoken to a child wearing wearable word counter 305 and a date axis 465 representative of a date. As shown in FIG. 4, each date on date axis 465 has an associated representation of a number of words spoken to a child associated with wearable word counter 305 on a per-day basis. For example, on July 1, a child wearing wearable word counter 305 heard approximately 2000 words directed at the child during the day of July 1.

Word count element 410 may further include one or more interface elements 470 which allow a user of graphical user interface 400 to scale date axis 465. Exemplary interface elements 470 include a button to scale date axis 465 to show a monthly word count total, a yearly word count total, a life word count total for the life of the wearer of wearable word counter 305, or an average number words directed at the wearer of wearable word counter 305. Other interface elements 470 may include a button to scale date axis 465 to show a weekly total of words spoken to the wearer of wearable word counter 305 or may allow a user to selectively scale date axis 465 to a specific selectable customized time period between two different user selected dates.

TV time element 415 may include a graphical representation of the number of minutes a child has spent watching television as identified by wearable word counter 305, shown in FIG. 3. TV time element 415 may include a minutes axis 445 representative of a number of minutes and a date axis 450 representative of a date. As shown in FIG. 4, each date on date axis 450 has an associated representation of a number of minutes a child associated with wearable word counter 305 has spent watching television on a per-day basis. For example, on July 1, a child wearing wearable word counter 305 watches television for approximately 60 minutes during the day of July 1.

TV time element 415 may further include one or more interface elements 455 which allow a user of graphical user interface 400 to scale date axis 450. Exemplary interface elements 455 include a button to scale date axis 450 to show a monthly total of television viewing time in minutes, a yearly total television viewing time in minutes, a life total of television viewing time in minutes for the life of the wearer of wearable word counter 305, or an average number of television viewing time in minutes for the wearer of wearable word counter 305. Other interface elements 455 may further include a button to scale date axis 450 to show a weekly total of television time in minutes or may allow a user to selectively scale date axis 450 to a specific selectable customized time period between two different user selected dates.

Sleep duration element 420 may include a graphical representation of the number of hours (as shown in FIG. 4 but may alternatively be shown in terms of minutes) a child associated with wearable counter 305, shown in FIG. 3 has slept. Sleep duration element 420 may include a time axis 475 representative of an amount of time and a date axis 480 representative of a date. As shown in FIG. 4, each date on date axis 480 has an associated representation of an amount of time that a child associated with wearable word counter 305 (i.e., a wearer of wearable word counter 305) has slept on a per-day basis. For example, on July 1, a child wearing wearable word counter 305 slept for approximately 8 total hours.

Sleep duration element 420 may further include one or more interface elements 485 which allow a user of graphical user interface 400 to scale date axis 480. Exemplary interface elements 485 include a button to scale date axis 480 to show a number of hours and minutes a child slept in a month, a number of hours and minutes a child slept in a year, a number of hours and minutes a child slept in a lifetime, or an average number of hours and minutes a child sleeps during a day. Other interface elements 440 may include a button to scale date axis 480 to show a weekly number of hours and minutes of sleep a wearer of wearable word counter 305 sleeps in a week or may allow a user to selectively scale date axis 480 to a specific selectable customized time period between two different user selected dates.

Reading duration and score element 425 may include a graphical representation of a reading duration and a reading score for a number of reading sessions. A reading session may include, for example, a parent reading a book to a child. In one embodiment, a score may be generated for each reading session by assessing the quality of the reading session in addition to the duration of the reading session on a per-day basis. As shown in FIG. 4, reading duration and score element 425 includes a score axis 490a representative of a score for a reading session and a duration axis 490b representative of a duration in minutes of a reading session. Reading duration and score element 425 further includes a date axis 495a and a date axis 495b representative of a particular date on which a reading session takes place. As shown in FIG. 4, each date on date axis 490a includes a graphical representation of an associated score for a reading session while each date on date axis 495b includes a graphical representation of a duration for a particular reading session that occurred on that date. For example, on July 1, a child wearing wearable word counter 305 participated in a reading session with a duration of approximately 30 minutes which was quite engaging for the child, resulting in a reading quality score of 95.

Reading duration and score element 425 may further include one or more interface elements 495c which allow a user of graphical user interface 400 to scale date axis 495a and date axis 495b. Exemplary interface elements 495c include a button to scale date axis 495a and date axis 495c to show a monthly duration and score for reading sessions in that month, a yearly total duration and score for reading sessions in that year, a life total duration and score for reading sessions for the lifetime of a child associated with wearable word counter 305, or an average duration and score of a reading sessions associated with a wearer of wearable word counter 305. Other interface elements 495c may include a button to scale date axis 495a and date axis 495b to show a weekly total of active minutes or may allow a user to selectively scale date axis 495a and date axis 495b to a specific selectable customized time period between two different user selected dates.

A health care provider (doctor, therapist, etc.) may access the information shown in graphical user interface 400 to get a general sense for a child's environment, activity level, and educational stimulation. Based on the information provided in graphical user interface 400, a health care provider may be better prepared to address specific issues associated with a child and may provide parents with feedback for improving a child's health.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A system, comprising:
a wearable device generating child activity data,
wherein the wearable device includes an analog input that includes a microphone for receiving input representative of human speech and transforming the input representative of human speech into a signal;
wherein the device detects one or more instances where the signal exceeds a threshold and identifies each instance where the signal exceeded the threshold as a spoken syllable and, based on the number of spoken syllables, determines a word count for the number of words received in the input representation of human speech,
one or more server devices analyzing the child activity data to determine an activity level of a wearer of the wearable device and transmit activity level data for graphical display on a health care provider device, and
wherein determining the activity level of a wearer includes determining the number of words received by the wearable device in the input representative of human speech.

2. The system of claim 1, wherein the wearable device includes a microphone.

3. The system of claim 1, wherein the wearable device includes an accelerometer.

4. The system of claim 1, wherein the wearable device includes a light sensor.

5. The system of claim 1, wherein the child activity data is generated based on information received via one or more of a microphone, an accelerometer, or a light sensor disposed within the wearable device.

6. The system of claim 1, wherein the activity level data transmitted for graphical representation on the health care provider device includes data representative of a duration of time in which the wearer of the wearable device is active on a per-day basis.

7. The system of claim 1, wherein the activity level data transmitted for graphical representation on the health care provider device includes data representative of a duration of time in which the wearer of the wearable device watches television a per-day basis.

8. The system of claim 1, wherein the activity level data transmitted for graphical representation on the health care provider device includes data representative of a word count of words spoken to the wearer of the wearable device on a per-day basis.

9. The system of claim 1, wherein the activity level data transmitted for graphical representation on the health care provider device includes data representative of a duration of time in which the wearer of the wearable device is asleep on a per-day basis.

10. The system of claim 1, wherein the activity level data transmitted for graphical representation on the health care provider device includes data representative of a duration of time in which the wearer of the wearable device is engaged in a reading session on a per-day basis.

11. The system of claim 10, wherein the activity level data transmitted for graphical representation on the health care provider device further includes data representative of a score of the reading session on a per-day basis.

12. The system of claim 1, further comprising:
 a secondary device receiving the child activity data and transmitting the child activity data to the one or more server devices.

13. The system of claim 12, wherein the secondary device is implemented as a smart phone.

14. The system of claim 12, wherein the secondary device is implemented as a tablet.

15. The system of claim 12, wherein the secondary device is implemented as a charging station.

\* \* \* \* \*